United States Patent [19]
Verstreken et al.

[11] Patent Number: 5,332,449
[45] Date of Patent: Jul. 26, 1994

[54] IMMERSION SENSOR FOR MOLTEN METALS

[75] Inventors: Paul C. Verstreken, Rotselaar-Heikant; Guido J. Neyens, Opoeteren, both of Belgium

[73] Assignee: Heraeus Electro-Nite International N.V., Antwerp, Belgium

[21] Appl. No.: 958,421

[22] Filed: Oct. 8, 1992

[30] Foreign Application Priority Data

Oct. 28, 1991 [DE] Fed. Rep. of Germany ....... 4135510

[51] Int. Cl.$^5$ .............................................. H01L 35/02
[52] U.S. Cl. ................................... 136/234; 136/201; 204/153.18; 204/421
[58] Field of Search ............... 136/200, 201, 233, 234; 374/179, 208, 180; 204/153.18, 421–429

[56] References Cited

U.S. PATENT DOCUMENTS

| | | | |
|---|---|---|---|
| 2,766,440 | 10/1956 | Marsden, Jr. | 340/228 |
| 3,116,168 | 12/1963 | Gee | 136/4 |
| 3,578,578 | 5/1971 | Krusenstierna | 204/195 |
| 4,035,277 | 7/1977 | Hennessy et al. | 204/195 S |
| 4,399,022 | 8/1983 | Nakajima et al. | 204/422 |
| 4,906,349 | 3/1990 | Beatrice et al. | 204/422 |
| 5,112,456 | 5/1992 | Worrell et al. | 204/153.18 |

FOREIGN PATENT DOCUMENTS

| | | |
|---|---|---|
| 60-53053 | 4/1985 | Japan . |
| 61-60154 | 4/1986 | Japan . |
| 2012428 | 7/1979 | United Kingdom . |
| 2167867 | 6/1986 | United Kingdom . |

*Primary Examiner*—Donald P. Walsh
*Assistant Examiner*—Chrisman D. Carroll
*Attorney, Agent, or Firm*—Panitch Schwarze Jacobs & Nadel

[57] ABSTRACT

An immersion sensor for molten metals has an electrically conducting support pin, whose one end is mounted in a refractory mounting material, and whose other free end has a first coating of a reference material and on top of this a second coating of a solid electrolyte material. The support pin has a third coating of a refractory material in the area of its mounted end, and this third coating on the one side extends into the mounting material, and on the other side extends into the solid electrolyte material. In order to obtain a quick reading and a stable EMF-value, the solid electrolyte material covers at least the end area of refractory coating nearest the free end of the support pin. A process for the manufacture of an intermediate for the immersion sensor applies the various coating materials of the immersion sensor in the order given above.

19 Claims, 5 Drawing Sheets

IMMERSION SENSOR FOR MOLTEN METALS

FIELD OF THE INVENTION

The invention relates to an immersion sensor for molten metals, wherein the sensor has an electrically conducting support pin whose one end is held in a refractory mounting material and whose other free end has a first coating of a reference material and thereupon a second coating of a solid electrolyte material. In the region of its mounted end the support pin has a third coating of a refractory material, which on the one side reaches into the mounting material and on the other side extends to the solid electrolyte material. The invention also relates to a method of making an intermediate for an immersion sensor.

BACKGROUND OF THE INVENTION

Such immersion sensors are known from JP-A1 61-60154. The immersion sensors, described therein, have a metal wire as a support pin, which at its one end is embedded into a mounting material. On its other end the support pin is also coated with a reference material of a metal-metal oxide. On top of this reference material is a layer of a solid electrolyte material. The support pin at its mounted end is coated with a refractory material, which on the one side reaches into the mounting material and on the other side extends to the solid electrolyte material, whereby the solid electrolyte material can be partially covered by the refractory material.

In such a construction the refractory material can corrode in the molten metal, whereby in the area outside of the mounting material where the refractory material touches the solid electrolyte material, the immersion sensor can change its electrochemical properties. As a result drastic changes occur in this area during the initial measuring phase of the EMF (electromotive force) measuring procedure, so that a constant EMF reading is only observed after a long immersion period or not at all. If there is an overlapping of the solid electrolyte material by the refractory material, then an additional EMF, which arises in an area extending below the refractory material, is being measured. This area is undefined and therefore leads to a distortion of the values when measuring the EMF.

A similar immersion sensor with the above described layer construction is also known from JP-A1 60-3053. With this construction also the above described inaccuracies occur.

In view of the above prior art it is the purpose of the present invention to produce an immersion sensor, which reaches a stable EMF-value after a short immersion period. An additional object of the invention is to develop a process for the manufacture of an intermediate for such an immersion sensor.

SUMMARY OF THE INVENTION

According to the invention the problems of the above-described prior art are solved by the solid electrolyte material covering at least the end area of the neighboring refractory material. By these means on the one hand, corrosion of the refractory material is avoided in an area where portions of the EMF to be measured act, and on the other hand the area in which the EMF is to be measured will be sharply defined. Therefore, the EMF to be measured will not suffer fluctuations for reasons of corrosion phenomena or undefined measuring areas. Even after a short immersion period, in which a thermal and electro-chemical equilibrium arises between the immersion sensor and the surrounding molten metal, a constant EMF-reading appears.

According to the method the problem is solved by placing on one end of a support pin a coating of a reference material, afterwards masking this end in such a way that the end opposite the reference material remains unmasked, providing on the unmasked part of the support pin a coating of refractory material, and after removing the masking placing on the reference material a coating of a solid electrolyte material, so that this coating covers the end of the refractory material coating which neighbors the end of the support pin. With this process it is possible to make an intermediate product for an immersion sensor which has the properties of the above described immersion sensor for molten metals, according to the invention.

The refractory material is preferably covered with a material which is corrosion-resistant in relation to the molten metal. For this purpose this corrosion-resistant material can be a solid electrolyte material, especially the same material as the solid electrolyte coating. Fluctuations in the corrosion-prone EMF are effectively suppressed by this means. In the case that the corrosion-resistant material is the same material as the solid electrolyte coating, the immersion sensor is very easily producible, since only one continuous layer of the material is to be applied.

Preferably, the refractory material starts at a distance of about 1 to 6 mm, especially at a distance of about 1.5 to 3.5 mm from the free end of the support pin, that is not the end embedded in mounting material. It has been shown that by this means the EMF to be measured lies in a relatively small, defined area along the immersion sensor. In this relatively small area, which is preferably about 2.5 mm long, the temperature fluctuations, which are implicit from the temperature gradients which might develop through the eventual immersion of the immersion sensor in the molten metal, are so small that the EMF, which is also dependent on the temperature of the molten metal, is practically not influenced by the temperature differences between the different (theoretical) measuring locations along the immersion sensor.

Preferably at least one of the layers, namely reference material, solid electrolyte material, refractory material and/or the corrosion-resistant material comprises a sprayed-on material, whereby an especially homogeneous and dense layer is achieved.

For this purpose the reference material comprises a metal-metal oxide, and the solid electrolyte material is preferably an oxygen ion conductor. Preferably, the reference material comprises chromium-chromium dioxide, and the solid electrolyte coating comprises stabilized zirconium oxide. By selecting these coating materials it is possible to measure the oxygen content in molten metals, especially in molten steel.

Preferably, the solid electrolyte coating has a higher density in the region of its outer side than in the region of the inner side which is near the support pin. Thereby the stability of the measurement is improved during a short reading period at a minimal layer thickness of the solid electrolyte coating.

It is advantageous for short measurements by the immersion sensor, and thereby for a fast reading time, that the support pin in the area of its free end have a maximum cross-sectional area between 0.1 mm$^2$ and 3 mm², especially between 0.3 mm² and 1.5 mm², and preferably about 0.8 mm². The cross-sectional area can have any shape, but is preferably round or oval.

Molybdenum has proved to be especially suitable as a material for the support pin due to its thermal properties.

In order to avoid too much heat loss through the support pin, the support pin can have a cross-sectional narrowing at least in the area of the refractory material coating.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there is shown in the drawings embodiments which are presently preferred, it being understood, however, that the invention is not limited to the specific arrangement and instrumentalities disclosed.

DETAILED DESCRIPTION OF PREFERRED EMBODIMENTS

Figure 1:
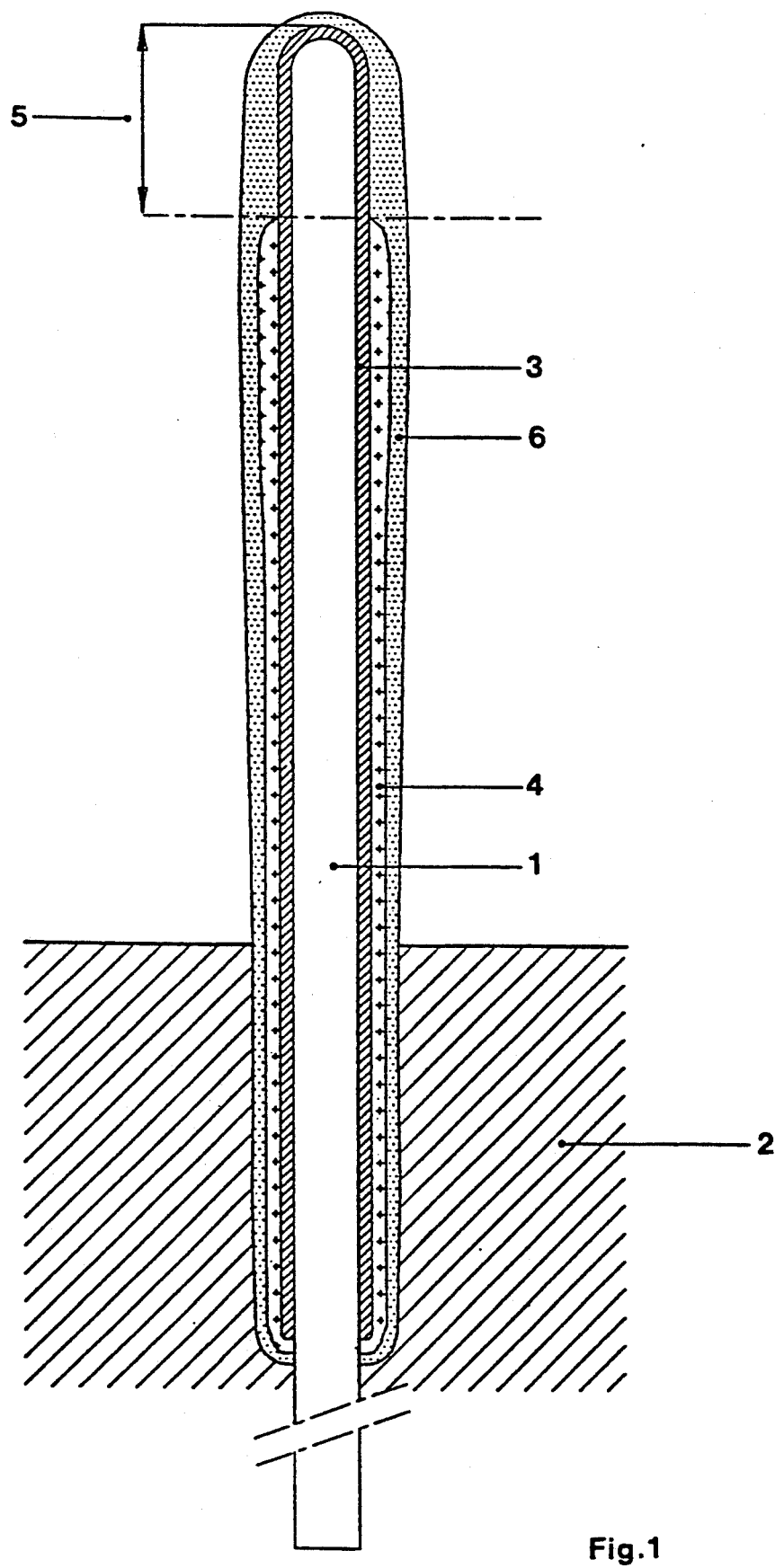
FIG. 1 is a schematic embodiment of the immersion sensor according to the invention.

The immersion sensor, as illustrated in FIG. 1, has a support pin 1, which serves as a shunt electrode and which is mounted at its one end in a refractory mass 2. The support pin has a cross-sectional area of 0.8 mm² and consists of molybdenum. The support pin 1 has on its surface a coating of a reference material 3 which extends into the refractory mounting material 2. The reference material 3 is chromium-chromium dioxide, which has been sprayed on at a coating thickness of about 200 µm. An aluminum oxide refractory material 4 covers the reference material 3 over such a length that this coating on the one side extends into the refractory mounting material 2 and on the other side covers the reference material 3 up to a distance 5 of about 2.5 mm from the free end of the support pin 1. The aluminum oxide refractory material 4 has a thickness of about 200 µm in the area lying outside of the refractory mounting material 2. The solid electrolyte material 6 is the third layer, which covers the reference material 3 and the refractory material 4 and extends into the refractory mounting material 2. The solid electrolyte material 6 consists of a stabilized zirconium oxide and has a layer thickness of about 300 µm.

The coatings 3, 4 and 6 which cover the support pin 1 can be applied by means of a spray-process, e.g., plasma-spraying or flame-spraying, which produces a very uniform and dense coating. First the chromium-chromium dioxide reference material 3 is applied to the support pin 1; then the end of the support pin 1 which has not been embedded is masked for a distance of about 2.5 mm; and then the aluminum oxide refractory material 4 is applied to the unmasked part of the support pin 1. Following that the masking is removed, and the stabilized zirconium oxide solid electrolyte material 6 is sprayed on. After spraying on the layers 3, 4 and 6, the support pin 1 is placed into the refractory mounting material 2 and is mounted there.

Figure 2:
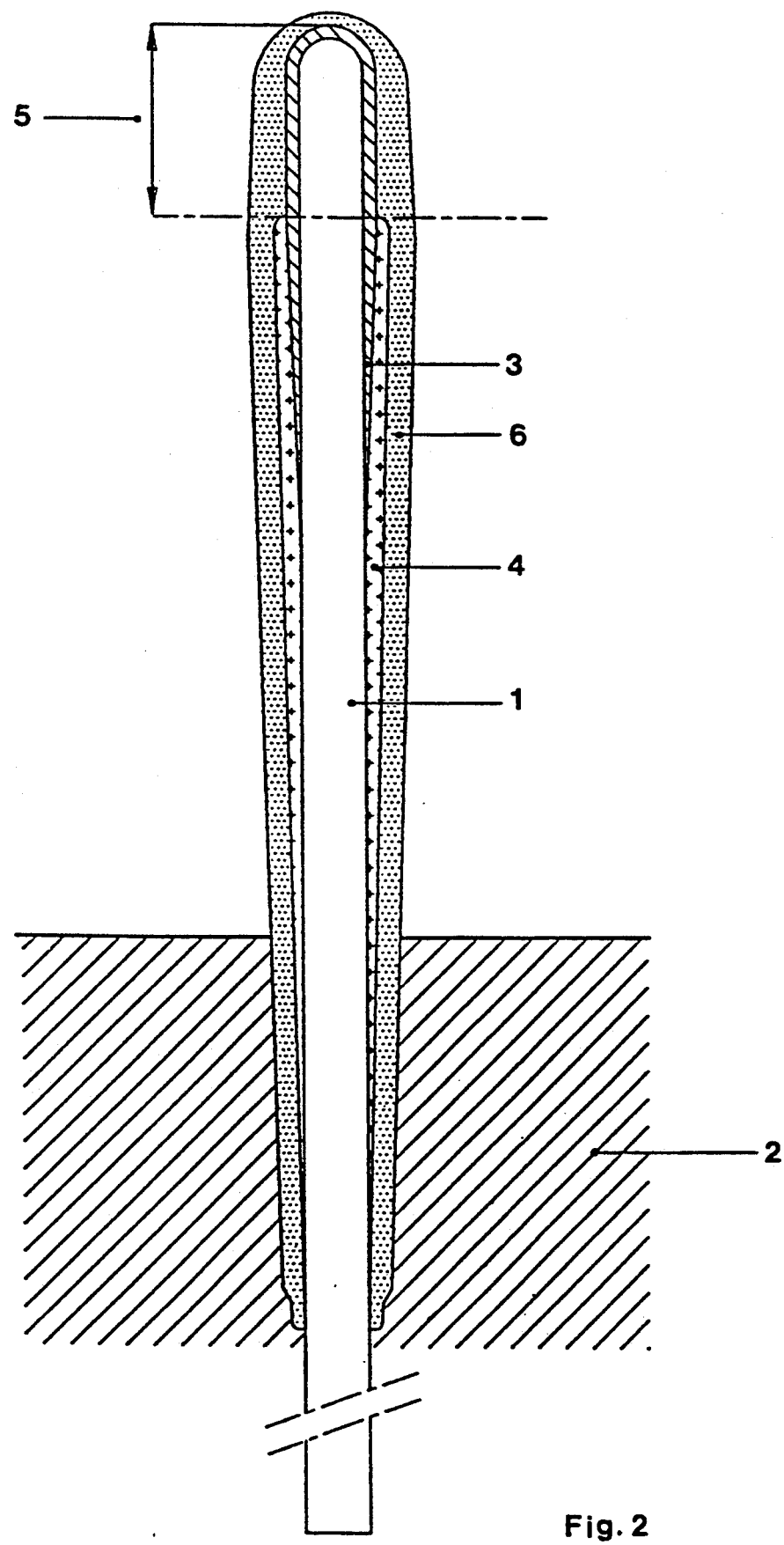
FIG. 2 is a further embodiment of an immersion sensor in which the reference material stretches over a shorter length in comparison to the embodiment of FIG. 1.

In FIG. 2, an immersion sensor is shown, which differs from the immersion sensor in FIG. 1, in that the reference material 3 does not extend into the refractory mass 2, but instead covers only the tip of the support pin 1 and ends under the refractory material 4. Therefore, as seen in cross-section, it ends in a wedge-shape. Such a coating is preferred for usage of an immersion sensor in the regions above 1645° C., since the otherwise unprotected chromium-chromium dioxide melts at this temperature, and thereby the mechanical stability of the immersion sensor could be lost by a further extension of the coating of the reference material 3 into the refractory mounting material 2.

An electro-chemical equilibrium between the molten metal and the immersion probe is necessary for an exact measurement of the EMF-value. However, an electro-chemical equilibrium only occurs if there is a thermal equilibrium between the immersion probe and its surroundings. In order to avoid loss of heat through the support pin 1, or to keep it as low as possible, it is necessary that the support pin 1 be as thin as possible. However, due to reasons of mechanical stability a certain minimum strength is needed. The optimal cross-sectional area of the support pin 1 is approximately 0.8 mm², which corresponds to a diameter of about 1 mm, if the support pin has a circular cross-section.

Figure 3:
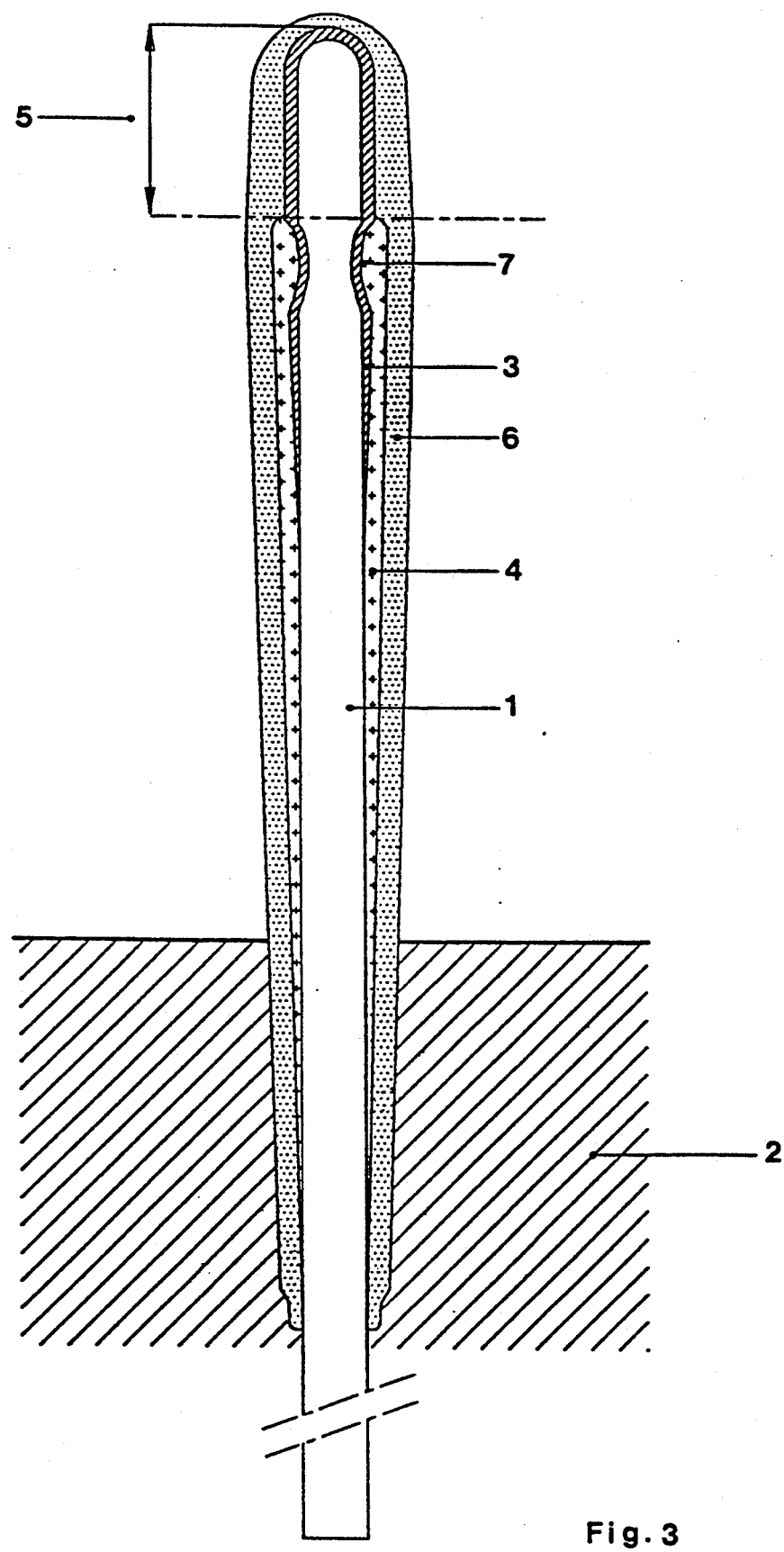
FIG. 3 shows an arrangement similar to that of FIG. 2 with a reduced diameter in the end area of the support pin.

For further reduction of heat loss it is in some cases possible and advantageous that the support pin 1 in the area of the aluminum oxide refractory material 4 have at least one circumferential cross-sectional narrowing 7, which reduces the loss of heat through the support pin 1 in the direction of the refractory mounting material 2. Such an embodiment of an immersion sensor is illustrated in FIG 3. The resulting cross-sectional area of the cross-sectional narrowing 7 is about half of the cross-sectional area of the support pin 1 in the region of the support pin 1 which is free of refractory material 4.

Figure 4:
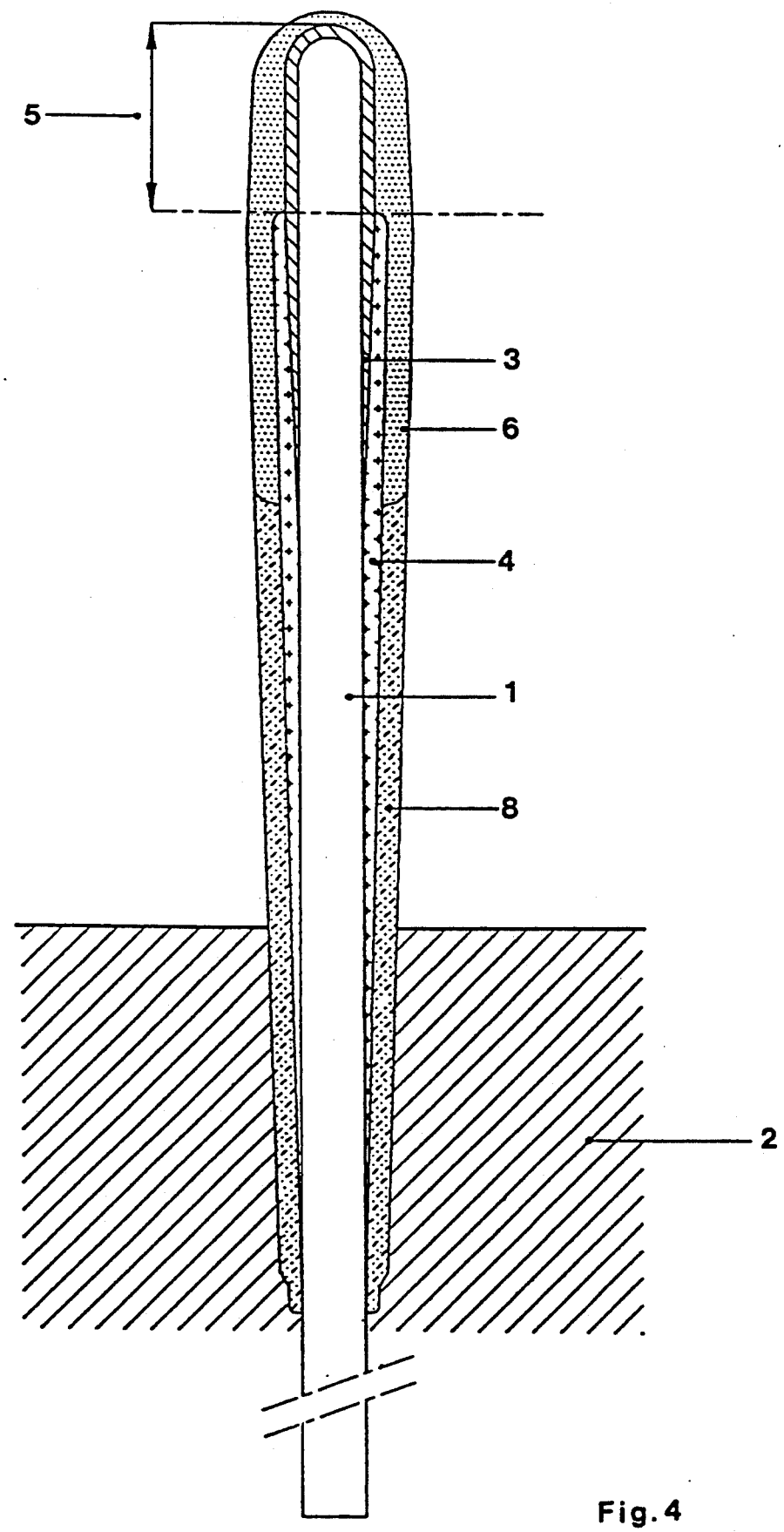
FIG. 4 shows an arrangement similar to that of FIG. 2 in which the forward area is coated with a stabilized zirconium dioxide, while the rear area has a different corrosion-resistant layer.

Another embodiment is shown in FIG. 4. In contrast to the embodiment shown in FIG. 2, the coating 6 of stabilized zirconium oxide is provided only on the forward area of the immersion sensor, so that the stabilized zirconium oxide covers only the end area of the refractory material 4. From the end of the layer 6 of stabilized zirconium oxide follows a layer of an additional corrosion-resistant material 8, which surrounds the refractory coating 4 of aluminum oxide, and extends into the refractory mounting material 2. This corrosion-resistant coating 8 comprises, e.g., silicates, borides, nitrides, carbides or oxides.

Figure 5:
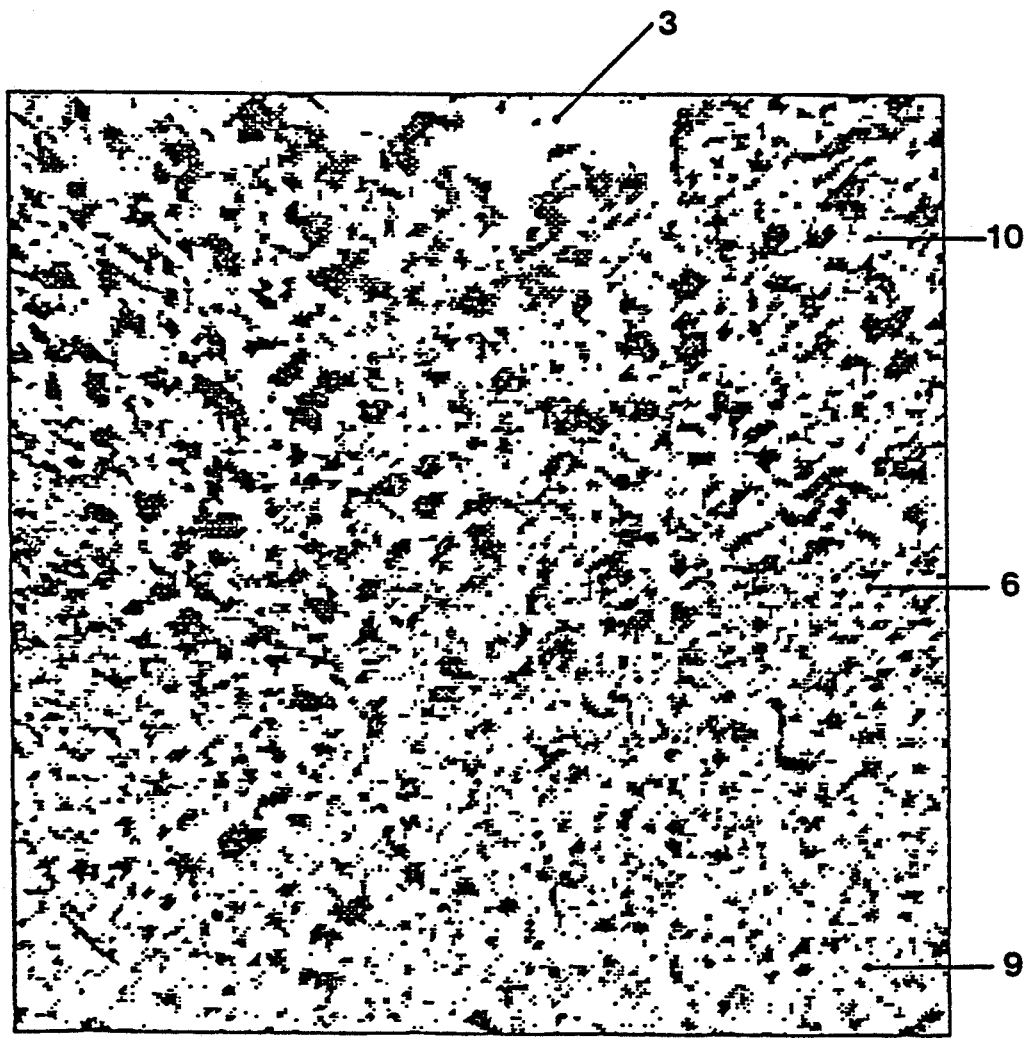
FIG. 5 is a representation of the porosity gradient within a zirconium oxide solid electrolyte material.

The porosity gradient within the solid electrolyte material 6 is shown in FIG. 5. The zirconium oxide has in the area of its outer side 9 a lower porosity, that is a higher density (displayed by the lighter areas) than in the area of its support pin, that is the inner side 10 (displayed by the darker areas) neighboring the reference material 3. With this porosity gradient the zirconium oxide is more corrosion-resistant on its outer side 9, and on the inner side 10 in the area neighboring the support pin, a faster ion exchange between the reference material 3 and the solid electrolyte material 6 is ensured.

In order to produce an intermediate of the immersion sensor, the one end of the support pin 1 of molybdenum is coated with reference material 3 of chromium-chromium dioxide. Afterwards, this end is masked for a distance 5 of about 2.5 mm from the end of the support pin, which is covered with reference material 3, in such a way that the end opposite from the reference material 3 remains unmasked. This unmasked part of the support pin 1 is coated with a refractory material 4 of aluminum oxide. Afterwards the masking is removed, and a coating of the solid electrolyte material 6 of stabilized zirconium oxide is placed on the reference material 3, so that this coating covers at least the end of the coating of refractory material 4 which is nearest the free end of the support pin 1.

The present invention may be embodied in other specific forms without departing from the spirit or essential attributes thereof and, accordingly, reference should be made to the appended claims, rather than to the foregoing specification as indicating the scope of the invention.

We claim:

1. An immersion sensor for molten metals, comprising an electrically conductive support pin (1), one end of said pin being mounted in a refractory mounting material (2) and the other end being free, said free end having a first coat of a reference material (3) and thereover a second coat of a solid electrolyte material (6); said pin further having in the area of its mounted end a third coat of a refractory material (4), said third coat on the one side extending into said mounting material (2) and on the other side extending into the solid electrolyte material (6), whereby the solid electrolyte material (6) covers at least the end area of the refractory material (4) nearest the free end of said pin, and the free end is uncoated with refractory material for a distance which is large enough to measure the EMF which arises between the sensor and molten metal upon immersion, said distance being small enough that temperature differences along the distance do not practically influence the measured EMF.

2. An immersion sensor according to claim 1 wherein the refractory material (4) is coated with a material (8) which is corrosion-resistant in relation to molten metal.

3. An immersion sensor according to claim 2 wherein the corrosion-resistant material (8) is a solid electrolyte.

4. An immersion sensor according to claim 3 wherein the corrosion-resistant material (8) is the same material as the solid electrolyte coating (6).

5. An immersion sensor according to claim 1 wherein the refractory material (4) begins at a distance of about 1 to 6 mm from the free end of the support pin (1).

6. An immersion sensor according to claim 5 wherein the distance is about 1.5 to 3.5 mm.

7. An immersion sensor according to claim 6 wherein the distance is about 2.5 mm.

8. An immersion sensor according to claim 1 wherein the reference material (3) and the solid electrolyte material (6) comprise a sprayed-on material.

9. An immersion sensor according to claim 1 wherein the refractory material (4) comprises a sprayed-on material.

10. An immersion sensor according to claim 2 wherein the corrosion-resistant material (8) comprises a sprayed-on material.

11. An immersion sensor according to claim 1 wherein the reference material (3) comprises a metal-metal oxide and the solid electrolyte material (6) comprises an oxygen ion conductor.

12. An immersion sensor according to claim 11 wherein the reference material (3) comprises chromium-chromium dioxide and the solid electrolyte coating (6) comprises stabilized zirconium oxide.

13. An immersion sensor according to claim 1 wherein the solid electrolyte coating (6) has in the area of its outer side (9) a higher density than in the area of its inner side (10) neighboring the support pin (1).

14. An immersion sensor according to claim 1 wherein the support pin (1) has in the area of its free end a maximum cross-sectional area, said area being about 0.1 mm$^2$ to 3 mm$^2$.

15. An immersion sensor according to claim 14 wherein the cross-sectional area is about 0.3 mm$^2$ and 1.5 mm$^2$.

16. An immersion sensor according to claim 15 wherein the cross-sectional area is about 0.8 mm$^2$.

17. An immersion sensor according to claim 1 wherein the support pin (1) comprises molybdenum.

18. An immersion sensor according to claim 1 wherein the support pin (1) has in the area of the coating of refractory material (4) at least one cross-sectional narrowing.

19. Process for the manufacture of an intermediate for an immersion sensor for molten metals, comprising coating a reference material (3) on one end of the support pin (1), masking said one end to such an extent that the reference material (3) on the part of said pin (1) away from said one end remains unmasked, coating on the unmasked part of said pin (1) a refractory material (4), removing the masking, and coating a solid electrolyte material (6) on top of the reference material (3), whereby said solid electrolyte coating covers the end of the refractory material coating (4) nearest said one end of support pin (1).

* * * * *